United States Patent
Mihara et al.

(10) Patent No.: US 10,203,301 B2
(45) Date of Patent: Feb. 12, 2019

(54) GAS SENSOR

(71) Applicant: NGK SPARK PLUG CO., LTD., Nagoya-shi, Aichi (JP)

(72) Inventors: Shunya Mihara, Komaki (JP); Takehiro Oba, Konan (JP); Shogo Nagata, Komaki (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 0 days.

(21) Appl. No.: 15/618,340

(22) Filed: Jun. 9, 2017

(65) Prior Publication Data
US 2017/0370877 A1   Dec. 28, 2017

(30) Foreign Application Priority Data
Jun. 22, 2016  (JP) ................. 2016-123471

(51) Int. Cl.
*G01N 27/40*   (2006.01)
*G01N 27/416*   (2006.01)
*G01N 33/00*   (2006.01)
*G01N 27/407*   (2006.01)

(52) U.S. Cl.
CPC ..... *G01N 27/4162* (2013.01); *G01N 27/4077* (2013.01); *G01N 33/0037* (2013.01)

(58) Field of Classification Search
CPC .................................................... G01N 27/40
See application file for complete search history.

(56) References Cited

U.S. PATENT DOCUMENTS

2005/0198810 A1* 9/2005 Taguchi ............. G01N 27/4077
29/592.1

FOREIGN PATENT DOCUMENTS

JP   2014-190846 A   10/2014

* cited by examiner

*Primary Examiner* — Son T Le
*Assistant Examiner* — Alex T Devito
(74) *Attorney, Agent, or Firm* — Stites & Harbison, PLLC; Jeffrey A. Haeberlin; James R. Hayne

(57) ABSTRACT

A gas sensor includes a sensor element having an electrode pad and a metal terminal member including a forward metal terminal member connected to the electrode pad, and a rear metal terminal member connected to the forward metal terminal member and a lead wire. The rear metal terminal member includes a forward end portion, a central portion, and a lead-wire connection portion. The forward end portion and the central portion are integrally connected through a first neck portion smaller in sectional area than the forward end portion and the central portion. The central portion and the lead-wire connection portion are integrally connected through a second neck portion smaller in sectional area than the central portion and the lead-wire connection portion. The first neck portion is greater in moment of inertia of area than the second neck portion.

4 Claims, 11 Drawing Sheets

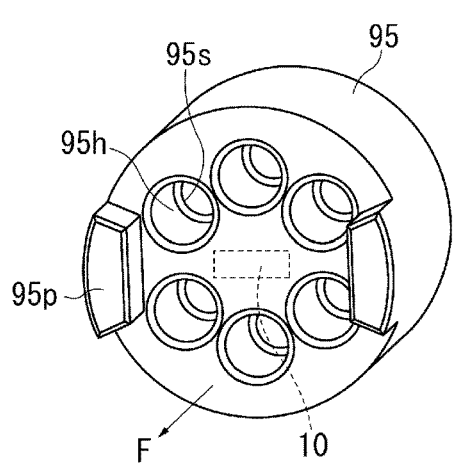
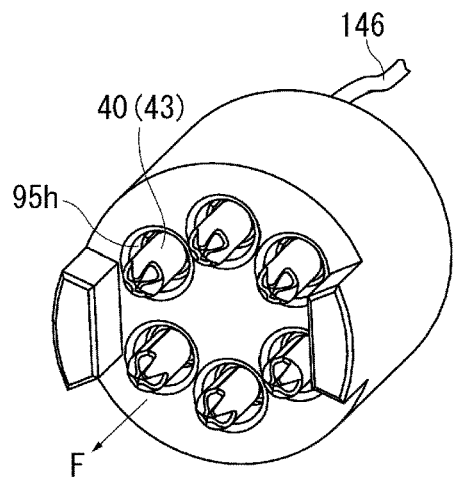
FIG. 7(a)  FIG. 7(b)
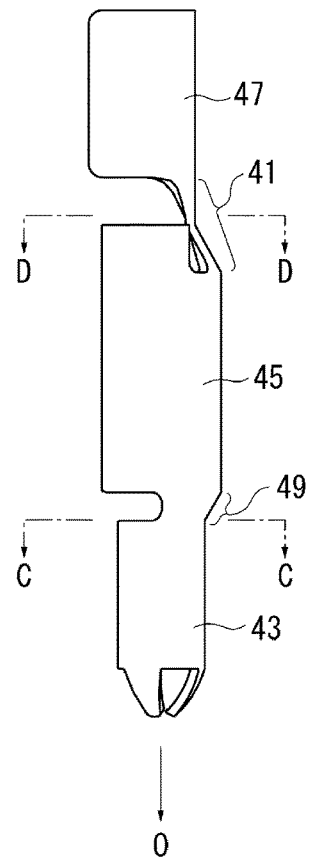
FIG. 8

US 10,203,301 B2

GAS SENSOR

CROSS REFERENCE TO RELATED APPLICATION

The present application claims priority to Japanese Patent Application No. 2016-123471, which was filed on Jun. 22, 2016, the disclosure of which is herein incorporated by reference in its entirety.

BACKGROUND OF THE INVENTION

Field of the Invention

The present invention relates to a gas sensor having a sensor element for detecting the concentration of a particular gas to be detected.

Description of Related Art

A known gas sensor for detecting the concentration of oxygen or $NO_x$ in exhaust gas of an automobile or the like has a plate-like sensor element which uses solid electrolyte.

In such a gas sensor, in order to output a signal indicative of the concentration of a particular gas to be detected to external equipment, metal terminal members are brought in contact with respective electrode pads provided on a rear end portion of a sensor element for electrical connection therebetween, and lead wires are crimped to respective rear-end crimp portions of the metal terminal members. The metal terminal members are held in a separator formed of an electrically insulative material, and the lead wires extend outward from the rear end of the separator to the outside of the gas sensor through a grommet.

Each lead wire is connected (crimped) to the corresponding metal terminal member as follows. First, the lead wire is inserted through the grommet and through an insertion hole of the separator such that a distal end portion of the lead wire appears on the forward side of the separator. Next, the distal end portion of the lead wire is crimped at a crimp portion of the metal terminal member disposed forward of the separator to thereby connect the lead wire to the metal terminal member.

Then, the lead wire is pulled rearward from the rear side of the grommet; accordingly, the metal terminal member connected to the lead wire is also pulled rearward to thereby be disposed within the separator.

However, since the lead wire is soft, difficulty is encountered in inserting the lead wire through the grommet and through the separator. Further, if the lead wire is inserted through the grommet and through the separator with conductors (strands) of the lead wire loosened, the loosened portion may cause defective insulation or conduction.

Thus, as shown in FIG. 12, there has been developed a technique in which the metal terminal member is divided into two pieces; specifically, a lead-wire connection member 210 formed of metal and having a diameter smaller than that of a through hole 300h of a grommet 300, and an element connection member 200 to be connected to a sensor element (Patent Document 1). A distal end portion of a lead wire 146 is connected, by crimping, to a rear portion 210b of the lead-wire connection member 210, while a forward portion 210a of the lead-wire connection member 210 is inserted into a rear tubular holding portion 200e of the element connection member 200, thereby establishing electrical connection therebetween.

According to this technique, the lead-wire connection member 210 serves as a guide for easily inserting the lead wire 146 through the through hole 300h of the grommet 300.

RELATED ART DOCUMENT

Patent Document 1 is Japanese Patent Application Laid-Open (kokai) No. 2014-190846 (FIG. 3).

BRIEF SUMMARY OF THE INVENTION

Since a narrow neck portion 210n exists between the forward portion 210a and the rear portion 210b of the lead-wire connection member 210, if the rigidity of the neck portion 210n is excessively low, in inserting the forward portion 210a into the holding portion 200e of the element connection member 200, the neck portion 210n may bend with a resultant change in the direction of the forward portion 210a, resulting in difficulty in insertion into the holding portion 200e. In contrast, if the rigidity of the neck portion 210n is excessively high, misalignment, if any, between the forward portion 210a and the rear portion 210b with respect to the axial direction may cause application of excessive force, within the through hole 300h, to the lead wire 146 crimped to the rear portion 210b, potentially resulting in detachment of the lead wire 146 from the rear portion 210b or breakage of the lead wire 146.

Thus, an object of the present invention is to provide a gas sensor in which two separate members of a metal terminal member can be reliably connected to each other and which is free from detachment of a lead wire from the metal terminal member and breakage of the lead wire.

In order to solve the above problem, a gas sensor of the present invention comprises a sensor element extending in a direction of an axial line and having an electrode pad on an outer surface of a rear end portion thereof; a metal terminal member extending in the direction of the axial line and electrically connected to the electrode pad; a tubular separator which holds the metal terminal member and surrounds the rear end portion of the sensor element; and a lead wire connected to a rear end portion of the metal terminal member and extending rearward of the separator. The metal terminal member has a forward metal terminal member electrically connected to the electrode pad, and a rear metal terminal member connected directly or indirectly to a distal end portion of the lead wire, and is configured such that a forward end portion of the rear metal terminal member is connected to a rear-end connection portion of the forward metal terminal member in an overlapping manner. The rear metal terminal member integrally has a central portion located rearward of the forward end portion, and a lead-wire connection portion located rearward of the central portion and connected to the lead wire. The forward end portion and the central portion are integrally connected through a first neck portion smaller in sectional area orthogonal to the direction of the axial line than the forward end portion and the central portion, and the central portion and the lead-wire connection portion are integrally connected through a second neck portion smaller in sectional area orthogonal to the direction of the axial line than the central portion and the lead-wire connection portion. The first neck portion is greater in moment of inertia of area than the second neck portion.

According to this gas sensor, by virtue of provision of the central portion, the forward end portion and the lead-wire connection portion can be connected through the central portion with the first neck portion and the second neck portion intervening therebetween, and the neck portions can be changed in moment of inertia of area (rigidity).

Thus, the first neck portion can be rendered higher in rigidity than the second neck portion. As a result, in connecting the forward end portion of the rear metal terminal member to the connection portion of the forward metal terminal member, there can be restrained difficulty in connection which could otherwise result from a change in direction of the forward end portion caused by bending of the first neck portion.

Meanwhile, the second neck portion is lower in rigidity than the first neck portion. As a result, in the case where the lead-wire connection portion is misaligned from the central portion and the forward end portion with respect to the direction of the axial line, excessive force may be applied to the lead wire connected to the lead-wire connection portion within an insertion hole of a rear separator. However, even in this case, since the second neck portion is deformed radially to thereby mitigate the force, there can be restrained detachment of the lead wire from the lead-wire connection portion and breakage of the lead wire.

In the gas sensor of the present invention, the forward end portion and the lead-wire connection portion of the rear metal terminal member may be coaxial in the direction of the axial line.

According to this gas sensor, misalignment between the lead-wire connection portion and the forward end portion with respect to the direction of the axial line reduces, whereby excessive force is unlikely to be applied to the lead wire connected to the lead-wire connection portion within an insertion hole of the rear separator, thereby restraining detachment of the lead wire from the lead-wire connection portion and breakage of the lead wire to a greater extent.

In the gas sensor of the present invention, the connection portion of the forward metal terminal member may assume the form of at least a portion of a tube (i.e., the rear-end connection portion of the forward metal terminal member is tube-like), and the forward end portion of the rear metal terminal member may taper off forward and be fitted into the rear-end connection portion.

According to this gas sensor, since the forward end portion tapers off forward, the forward end portion can be readily fitted into the tubular connection portion, whereby the rear metal terminal member and the forward metal terminal member can be easily and reliably connected to each other.

In the gas sensor of the present invention, the forward end portion of the rear metal terminal member may assume the form of at least a portion of a circular column or a cylinder (i.e., the forward end portion of the rear metal terminal member may be cylinder-like), and the connection portion of the forward metal terminal member may assume the form of at least a portion of a cylinder (i.e., the rear-end connection portion of the forward metal terminal member may be cylinder-like) and receive the forward end portion.

According to this gas sensor, since the connection portion and the forward end portion are of rotational symmetry about the axis, even though the rear metal terminal member and the forward metal terminal member are positionally deviated about the axis to some extent, the forward end portion can be fitted into the connection portion, whereby the rear metal terminal member and the forward metal terminal member can be easily and reliably connected to each other.

EFFECT OF THE INVENTION

The present invention provides a gas sensor in which two separate members of a metal terminal member can be reliably connected to each other and which is free from detachment of a lead wire from the metal terminal member and breakage of the lead wire.

BRIEF DESCRIPTION OF THE DRAWINGS

Illustrative aspects of the invention will be described in detail with reference to the following figures wherein:

FIGS. 7(a) and 7(b) are views showing a step of fitting the rear metal terminal members into a rear separator.

FIG. 8 is a side view of the rear metal terminal member.

DETAILED DESCRIPTION OF EXEMPLARY EMBODIMENTS OF THE INVENTION

An embodiment of the present invention will next be described.

Figure 1:
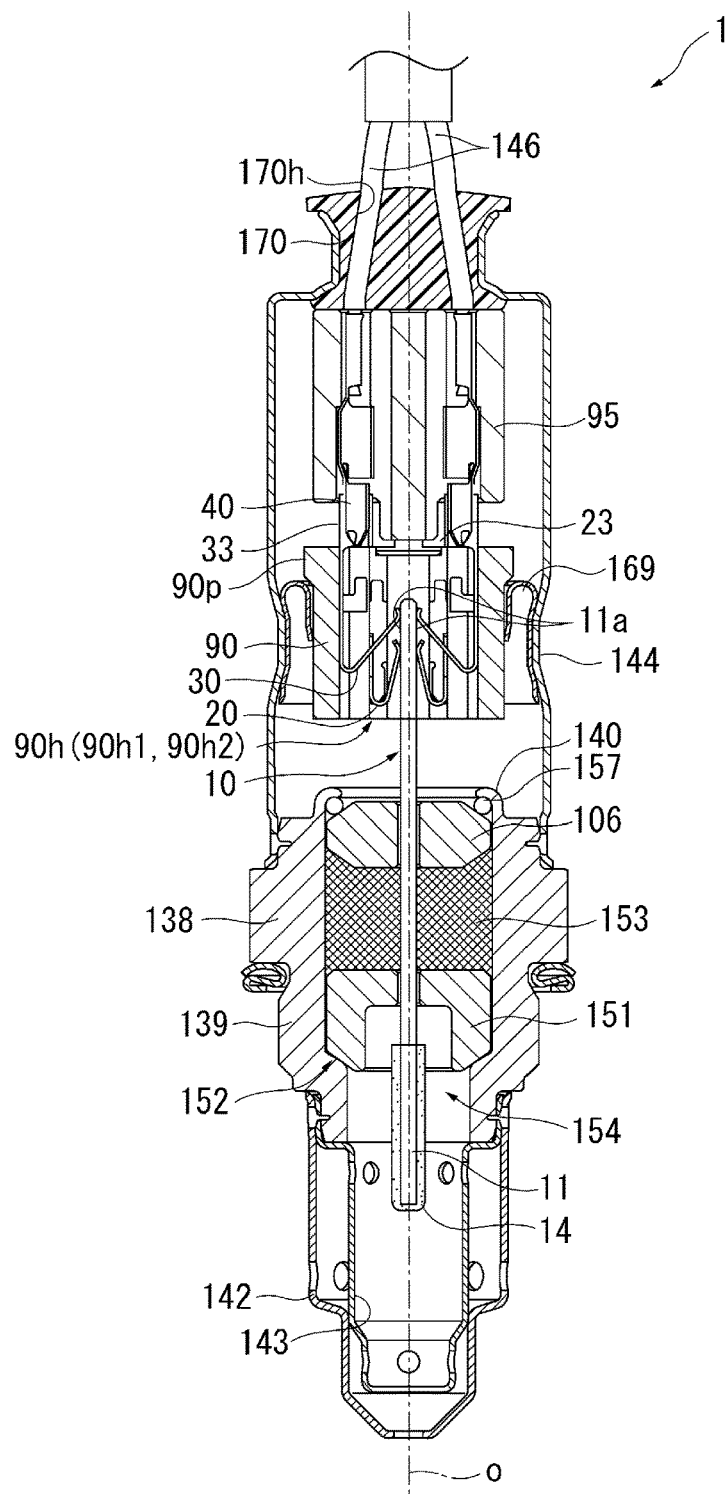
FIG. 1 is a sectional view of a gas sensor according to an embodiment of the present invention taken along an axial direction.
Figure 2:
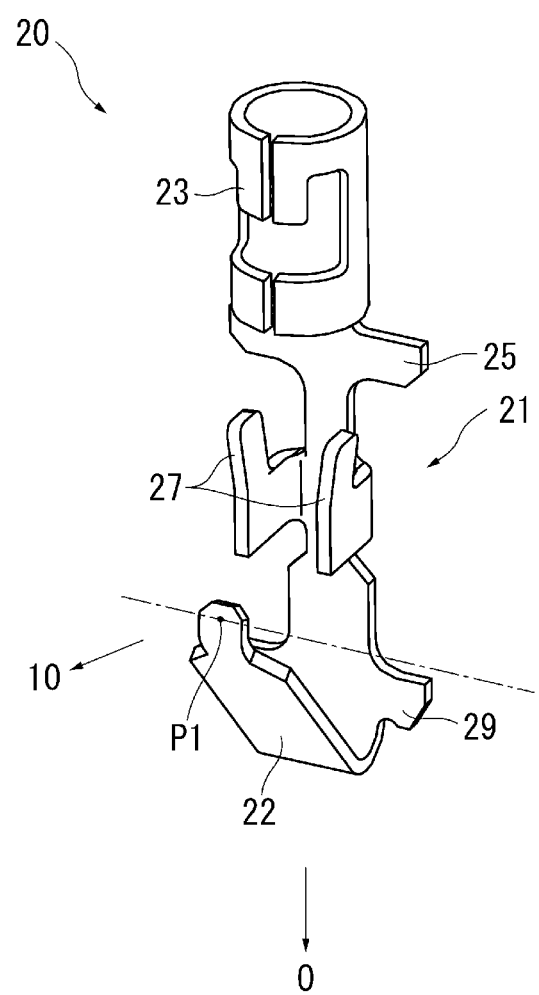
FIG. 2 is a perspective view of a forward metal terminal member.
Figure 3:
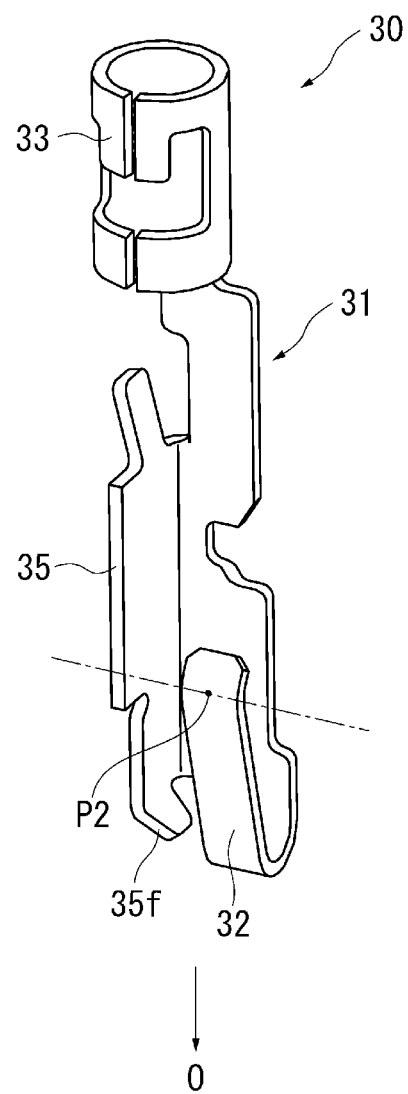
FIG. 3 is a perspective view of another forward metal terminal member.
Figure 4:
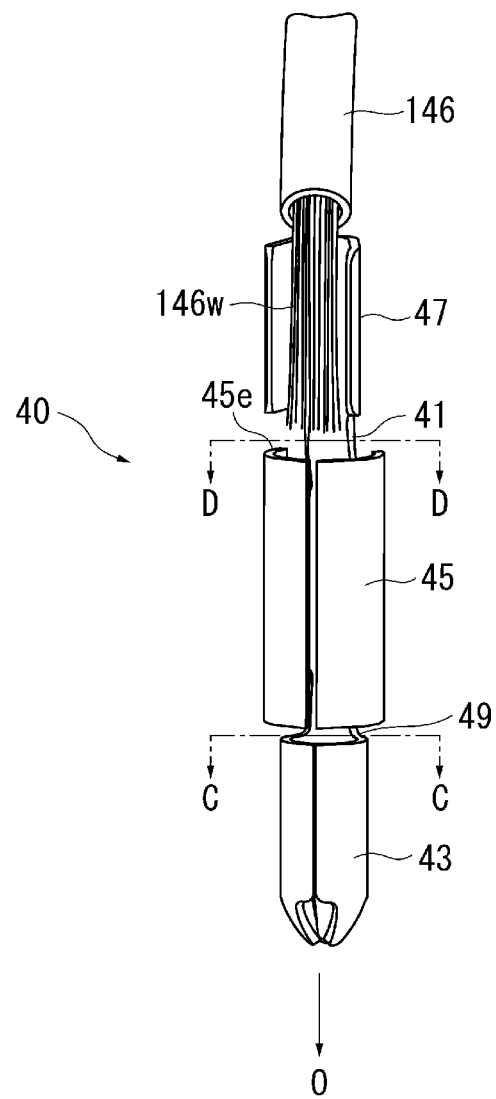
FIG. 4 is a perspective view of a rear metal terminal member.
Figure 5:
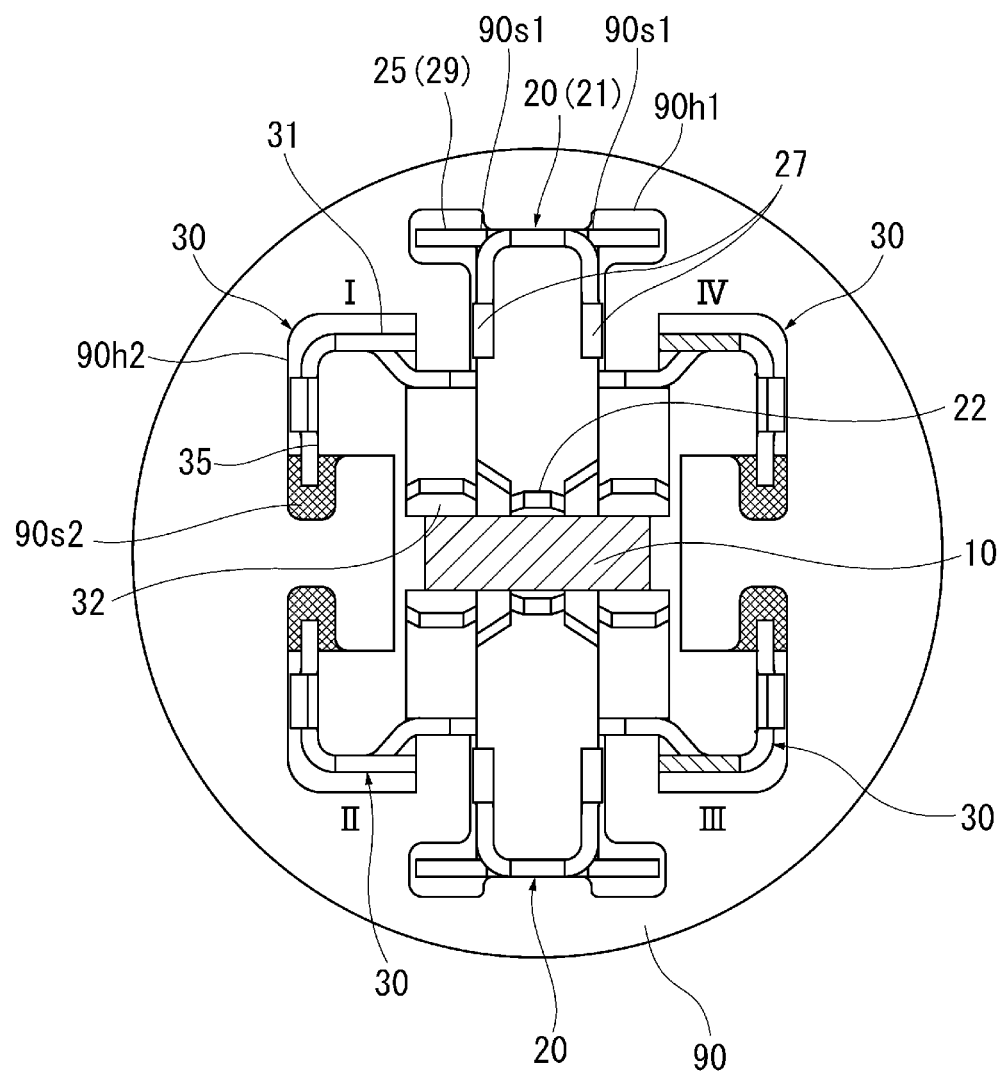
FIG. 5 is a sectional view showing a state in which the forward metal terminal members are held in a forward separator.
Figure 6A:
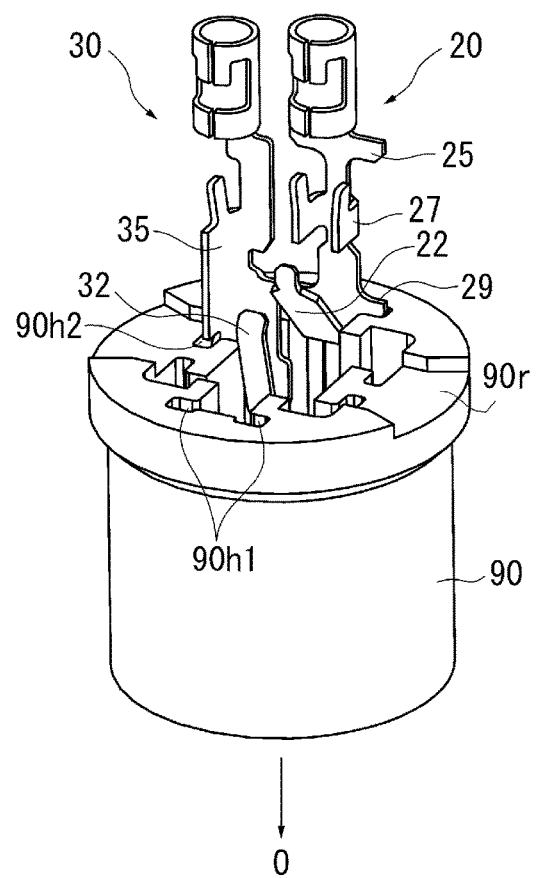
FIGS. 6(a) and 6(b) are views showing a step of fitting the forward metal terminal members into the forward separator.
Figure 6B:
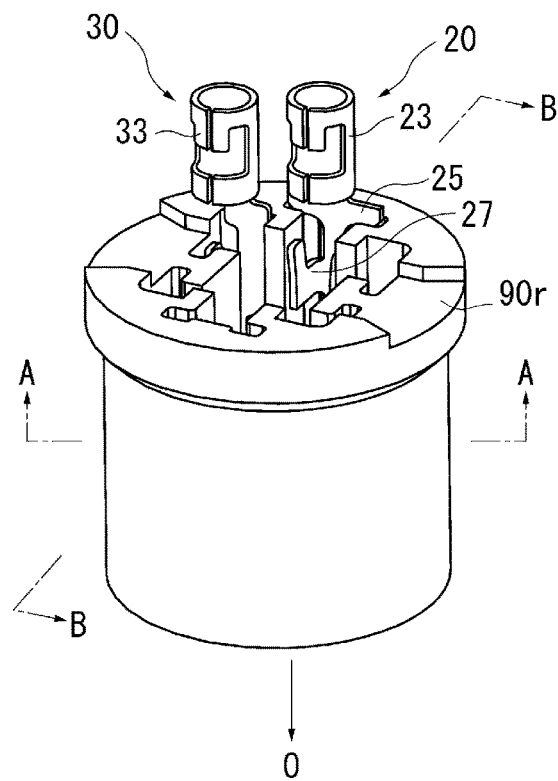

FIG. 1 is an overall sectional view of a gas sensor ($NO_x$ sensor) 1 according to an embodiment of the present invention taken along the direction of an axial line O; FIGS. 2 and 3 are perspective views of forward metal terminal members 20 and 30, respectively; FIG. 4 is a perspective view of a rear metal terminal member 40; FIG. 5 is a sectional view showing a state in which the forward metal terminal members 20 and 30 are held in a forward separator 90; FIGS. 6(a) and 6(b) are views showing a step of fitting the forward metal terminal members 20 and 30 into the forward separator 90; and FIGS. 7(a) and 7(b) are views showing a step of fitting the rear metal terminal members 40 into a rear separator 95.

The gas sensor 1 is an $NO_x$ sensor for detecting the concentration of oxygen in exhaust gas from automobiles and various internal combustion engines.

In FIG. 1, the gas sensor 1 includes a tubular metallic shell 138 having a threaded portion 139 formed on its outer surface and adapted for fixation to an exhaust pipe; a plate-like sensor element 10 extending in the direction of the axial line O (the longitudinal direction of the gas sensor 1, or the vertical direction in the drawing); a tubular ceramic sleeve 106 disposed in such a manner as to radially surround the sensor element 10; a tubular forward separator 90 made of ceramic and disposed in such a manner as to surround a rear end portion of the sensor element 10 inserted into a forward internal space thereof; six forward metal terminal members 20 and 30 (only four of them illustrated in FIG. 1) inserted into and held in insertion holes 90h (90h1 and 90h2) extending through the forward separator 90 in the direction of the axial line O; a tubular rear separator 95 made of ceramic; and six rear metal terminal members 40 (only two of them illustrated in FIG. 1) held in the rear separator 95.

As will be described later, the rear separator 95 is disposed on the rear side of and engaged with the forward separator 90.

An assembly of the forward separator 90 and the rear separator 95 corresponds to the "separator" appearing in claims.

As shown in FIG. 5, the insertion holes 90h1 and 90h2 of the forward separator 90 communicate with the above-mentioned forward internal space of the forward separator 90, and the forward metal terminal members 20 and 30 held in the insertion holes 90h1 and 90h2, respectively, face the outer surface of a rear end portion of the sensor element 10 and are electrically connected to respective electrode pads 11a formed on the outer surface.

Three electrode pads 11a are juxtaposed in the width direction of the sensor element 10 on each of opposite sides of the rear end portion of the sensor element 10. The electrode pads 11a can be formed of, for example, a sintered body which predominantly contains Pt.

Meanwhile, a forward-end gas detecting section 11 of the sensor element 10 is covered with a porous protection layer 14 of alumina or the like.

The metallic shell 138 is a generally tubular member formed of stainless steel and having a through hole 154 extending therethrough in the direction of the axial line and a ledge portion 152 protruding radially inward of the through hole 154. The sensor element 10 is disposed in the through hole 154 such that a forward end portion thereof protrudes from the forward end of the through hole 154. Further, the ledge portion 152 is tapered inward and inclined from a plane perpendicular to the direction of the axial line.

Within the through hole 154 of the metallic shell 138, a generally annular ceramic holder 151 made of alumina, a powder filler layer 153 (hereinafter, may be called the talc ring 153), and the above-mentioned ceramic sleeve 106 are stacked in this order from the forward side to the rear side in such a manner as to radially surround the sensor element 10.

Also, a crimp packing 157 is disposed between the ceramic sleeve 106 and a rear end portion 140 of the metallic shell 138. The rear end portion 140 of the metallic shell 138 is crimped in such a manner as to press the ceramic sleeve 106 forward through the crimp packing 157.

Meanwhile, as shown in FIG. 1, a dual protector made of metal (e.g., stainless steel) is attached, by welding or the like, to the outer circumference of a forward end portion (a lower portion in FIG. 1) of the metallic shell 138 and covers a protruding portion of the sensor element 10. The dual protector has a plurality of holes and consists of an outer protector 142 and an inner protector 143.

A sleeve 144 is fixed to the outer circumference of a rear end portion of the metallic shell 138. Lead wires 146 are connected to rear end portions of the rear metal terminal members 40, respectively, and extend rearward from the rear end of the rear separator 95.

A grommet 170 made of rubber is disposed in a rear-end (an upper-end in FIG. 1) opening portion of the sleeve 144 and has lead-wire insertion holes 170h into which six lead wires 146 (only two of them illustrated in FIG. 1) extending from the rear separator 95 are inserted respectively.

The forward separator 90 is disposed around a rear end portion (an upper end portion in FIG. 1) of the sensor element 10 protruding from the rear end portion 140 of the metallic shell 138 and has a collar portion 90p protruding radially outward from the outer surface thereof. The collar portion 90p is in contact with the sleeve 144 through a holding member 169, whereby the forward separator 90 is held within the sleeve 144.

The rear separator 95 is disposed between the grommet 170 and the forward separator 90, and elastic force of the grommet 170 causes the rear separator 95 to press forward the forward separator 90. As a result, the collar portion 90p is pressed against the holding member 169, whereby the forward separator 90 and the rear separator 95 are held within the sleeve 144 in a mutually connected condition (i.e., without separation in the direction of the axial line O).

FIGS. 2 and 3 are perspective views of the forward metal terminal members 20 and 30, respectively. The present embodiment uses forward metal terminal members of two types; specifically, the forward metal terminal members 20 and 30.

As shown in FIG. 5, since the four forward metal terminal members 30 are such that the forward metal terminal members 30 adjacent to each other in the forward separator 90 are axisymmetric in shape, one of the forward metal terminal members 30 (one located at upper left position I in FIG. 5) will be used for description.

The forward metal terminal member 30 located at lower left position II in FIG. 5 is axisymmetric to the forward metal terminal member 30 located at position I with respect to a line along a plane of the sensor element 10. The forward metal terminal member 30 located at lower right position III in FIG. 5 is axisymmetric to the forward metal terminal member 30 located at position II with respect to a line perpendicular to the plane of the sensor element 10. The forward metal terminal member 30 located at upper right position IV in FIG. 5 is axisymmetric to the forward metal terminal member 30 located at position I with respect to the line perpendicular to the plane of the sensor element 10.

The two forward metal terminal members 20 face each other in the forward separator 90 and are axisymmetric in shape; therefore, one of the forward metal terminal members 20 (one located at an upper position in FIG. 5) will be used for description.

The lower forward metal terminal member 20 in FIG. 5 is axisymmetric to the upper forward metal terminal member 20 with respect to the line along the plane of the sensor element 10. Each of the forward metal terminal members 20 is located between the two forward metal terminal members 30 with respect to the width direction of the sensor element 10.

As shown in FIG. 2, the forward metal terminal member 20 extends in the direction of the axial line O and integrally includes a connection portion 23 to be connected to the rear metal terminal member 40, a generally plate-like body portion 21 located forward of the connection portion 23, and an elastic portion 22 bent toward the sensor element 10 at the forward end of the body portion 21.

The forward metal terminal member 20 can be manufactured, for example, as follows: a blank is punched out from a single metal plate (INCONEL (registered trademark) or the like), and then the blank is bent to a predetermined shape. The manufacturing method is not limited thereto.

The connection portion 23 has a cylindrical tubular shape having a C-shaped section, and the rear metal terminal member 40 whose forward end portion has a cylindrical tubular shape having a C-shaped section is fitted into the connection portion 23. In this case, the forward metal terminal member 20 is indirectly connected to the lead wire 146 through the rear metal terminal member 40.

A portion of the body portion 21 at the center thereof with respect to the direction of the axial line O has wing portions on opposite sides with respect to the width direction thereof. The wing portions are bent 90 degrees toward the sensor element 10 side to thereby form a pair of holding portions 27 whose sections partially constitute a squarish-letter-U-shaped section. The body portion 21 serves as a base portion of the forward metal terminal member 20 for securing strength of the forward metal terminal member 20. The two holding portions 27 fan out rearward.

Also, a rear end portion of the body portion 21 located on the rear side with respect to the direction of the axial line O has a pair of quadrangular rear holding portions 25 which are flush with the body portion 21 and extend outward from opposite sides of the rear end portion of the body portion 21 with respect to the width direction thereof. Similarly, a forward end portion of the body portion 21 located on the forward side with respect to the direction of the axial line O has a pair of quadrangular forward holding portions 29 which are flush with the body portion 21 and extend outward from opposite sides of the forward end portion of the body portion 21 with respect to the width direction thereof.

The elastic portion 22 is bent rearward and toward the sensor element 10 from the forward end of the body portion 21 and is elastically connected to the electrode pad 11a (see FIG. 1) at a contact P1. The elastic portion 22 elastically bends radially in relation to the body portion 21.

As shown in FIG. 3, the forward metal terminal member 30 extends in the direction of the axial line O and integrally includes a connection portion 33 to be connected to the rear metal terminal member 40, a generally plate-like body portion 31 located forward of the connection portion 33, and an elastic portion 32 bent toward the sensor element 10 at the forward end of the body portion 31.

The forward metal terminal member 30 can be manufactured, for example, as follows: a blank is punched out from a single metal plate (INCONEL (registered trademark) or the like), and then the blank is bent to a predetermined shape. The manufacturing method is not limited thereto.

Similar to the connection portion 23, the connection portion 33 has a cylindrical tubular shape, and the rear metal terminal member 40 is fitted into the connection portion 33.

The body portion 31 has an L-shaped section and has a wing portion on one side with respect to the width direction of the body portion 31. The wing portion is bent 90 degrees toward the sensor element 10 side to thereby form a position holding portion 35. The body portion 31 serves as a base portion of the forward metal terminal member 30 for securing strength of the forward metal terminal member 30. A forward end portion 35f of the position holding portion 35 is bent inward in the width direction of the body portion 31 (toward the elastic portion 32).

The elastic portion 32 is bent rearward and toward the sensor element 10 from the forward end of the body portion 31 and is elastically connected to the electrode pad 11a (see FIG. 1) at a contact P2. The elastic portion 32 elastically bends radially in relation to the body portion 31.

Meanwhile, as shown in FIG. 4, the rear metal terminal member 40 extends in the direction of the axial line O and integrally includes, from the rear side, a crimp terminal portion 47 to be connected to the lead wire 146, a cylindrical tubular large-diameter portion 45 having a C-shaped section, and a cylindrical tubular forward end portion 43 having a C-shaped section.

The large-diameter portion 45 and the crimp terminal portion 47 correspond to the "central portion" and the "lead-wire connection portion" appearing in claims.

The rear metal terminal member 40 can be manufactured, for example, as follows: a blank is punched out from a single metal plate (SUS304 or the like), and then the blank is bent to a predetermined shape. The manufacturing method is not limited thereto.

The crimp terminal portion 47 crimps uncovered conductors 146w of a forward end portion of the lead wire 146 to thereby tubularly grip the conductors 146w.

The forward end portion 43 has a cylindrical tubular form and tapers off forward. The forward end portion 43 is fitted into the tubular connection portion 23 or 33, whereby the rear metal terminal member 40 is electrically connected to the forward metal terminal member 20 or 30.

The large-diameter portion 45 is greater in diameter than the crimp terminal portion 47 and the forward end portion 43, and a rear end face 45e of the large-diameter portion 45 is located radially outward of the crimp terminal portion 47.

Further, the forward end portion 43 and the large-diameter portion 45 are integrally connected through a first neck portion 49, and the large-diameter portion 45 and the crimp terminal portion 47 are integrally connected through a second neck portion 41.

As will be discussed in detail later, as shown in FIGS. 9 and 10, the area of section S1 orthogonal to the direction of the axial line O of the first neck portion 49 is smaller than the sectional areas orthogonal to the direction of the axial line O of the forward end portion 43 and the large diameter portion 45. Also, the area of section S2 orthogonal to the direction of the axial line O of the second neck portion 41 is smaller than the areas of section orthogonal to the direction of the axial line O of the large-diameter portion 45 and the crimp terminal portion 47.

As shown in FIG. 5, the forward separator 90 has the insertion holes 90h1 and 90h2.

The insertion holes 90h2 are disposed at four corners of the forward separator 90, and the insertion holes 90h1 are located between two insertion holes 90h2 along the width direction of the sensor element 10.

A rearward-facing surface 90s1 is formed on the forward side of the insertion holes 90h1, and a rearward-facing surface 90s2 is formed on the forward side of the insertion holes 90h2.

As shown in FIGS. 6(a) and 6(b), the forward metal terminal member 20 is inserted from the rear side into the insertion hole 90h1 (FIG. 6(a)) to thereby be held in the forward separator 90 (FIG. 6(b)).

Similarly, the forward metal terminal member 30 is inserted from the rear side into the insertion hole 90h2 (FIG. 6(a)) to thereby be held in the forward separator 90 (FIG. 6(b)).

In a state in which the forward metal terminal members 20 and 30 are held in the forward separator 90, the connection portions 23 and 33 protrude rearward from the forward separator 90 (FIG. 6(b)).

Meanwhile, as shown in FIGS. 7(a) and 7(b), the rear separator 95 has six circumferentially disposed insertion holes 95h. Each of the insertion holes 95h is large in diameter on the forward F side and reduces in diameter stepwise in the vicinity of the center with respect to the direction of the axial line O, and the resultant stepped portion forms a forward-facing surface 95s (FIG. 7(a)).

Two protrusions 95p protruding in the direction of the axial line O are formed at the periphery of the forward end surface of the rear separator 95. The protrusions 90p are engaged with the bottoms of recesses 90r of the forward separator 90.

The lead wire 146 is passed beforehand through the insertion hole 95h such that a distal end of the lead wire 146 appears on the forward side of the rear separator 95, and the distal end of the lead wire 146 is connected to the rear metal terminal member 40 on the forward side of the rear separator 95. Next, a portion of the rear metal terminal member 40 on the lead wire 146 side is inserted into the insertion hole 95h from the forward F side, and the lead wire 146 is pulled rearward. As a result, the rear end face 45e (see FIG. 4) of the large-diameter portion 45 of the rear metal terminal member 40 comes into contact with the forward-facing surface 95s, whereby the rear metal terminal member 40 is positioned and held in the rear separator 95 (FIG. 7(b)).

In this state, a forward portion of the forward end portion 43 (a portion of the forward end portion 43 located forward of the center with respect to the direction of the axial line O) of the rear metal terminal member 40 protrudes from the forward end surface of the rear separator 95.

Then, the forward separator 90 and the rear separator 95 shown in FIGS. 6(a) and 6(b) and FIGS. 7(a) and 7(b) are disposed relatively on the forward side and on the rear side, respectively, and connected together by engaging the protrusions 95p of the rear separator 95 with the recesses 90r of the forward separator 90.

Figure 11A:
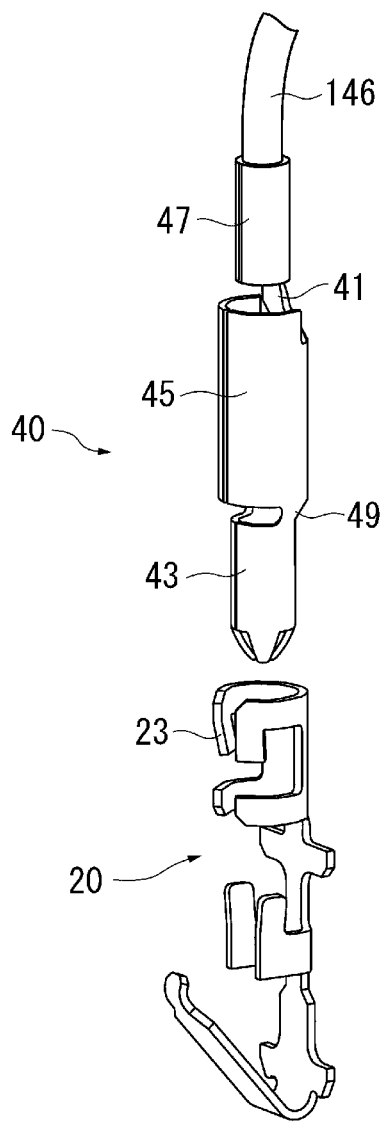
FIGS. 11(a) and 11(b) are views showing a step of connecting the forward metal terminal member and the rear metal terminal member.
Figure 11B:
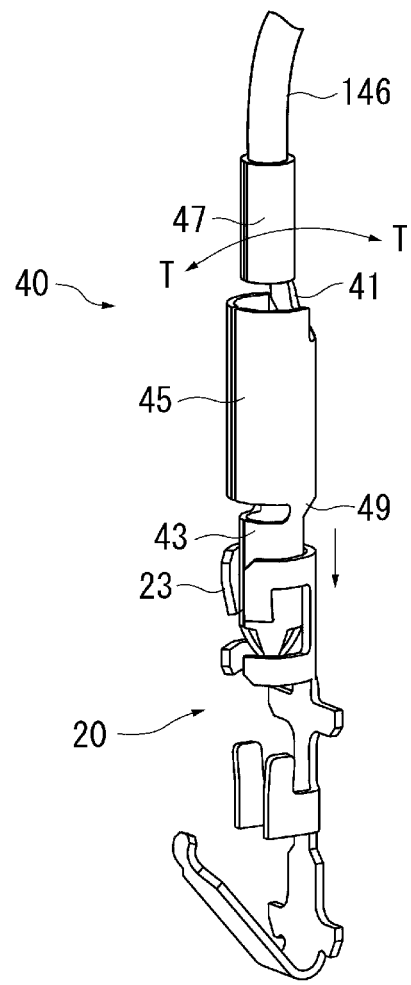
Figure 12:
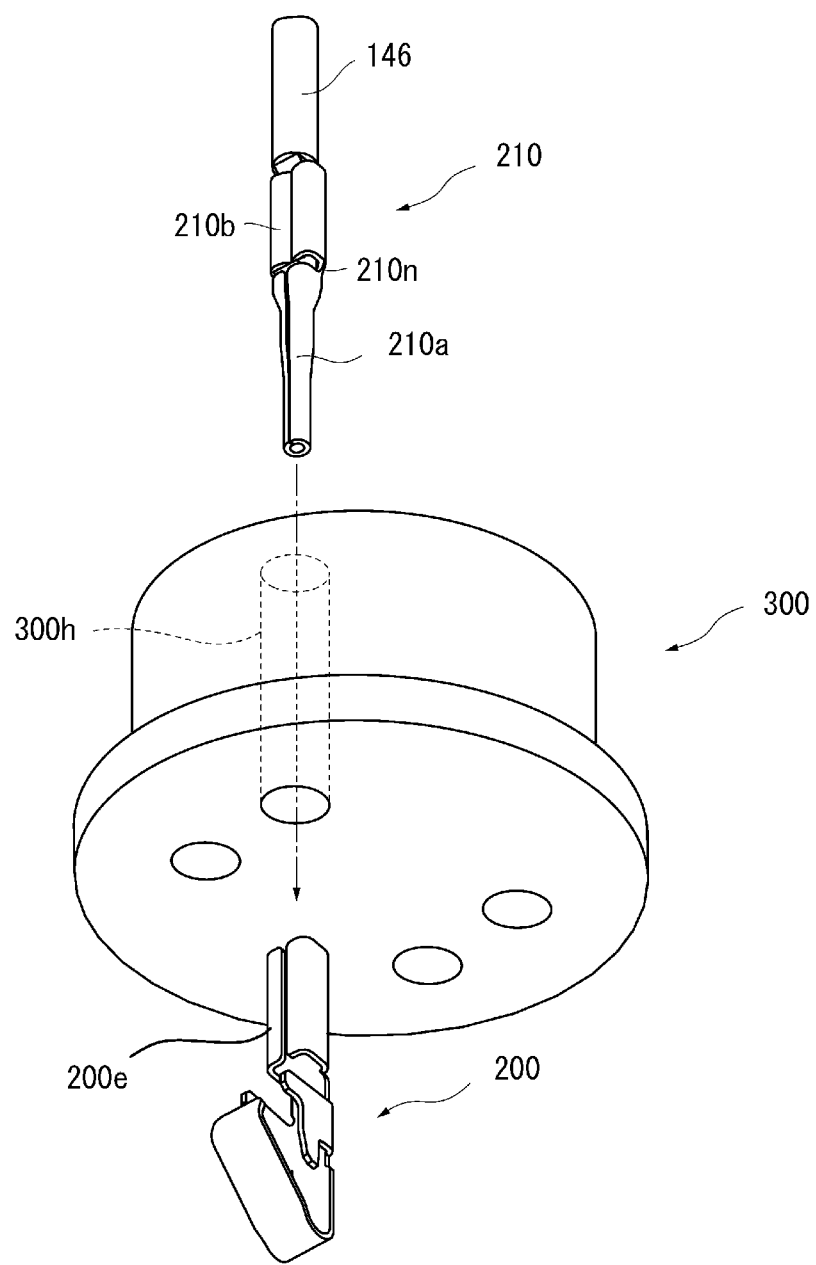
FIG. 12 is a perspective view showing insertion of a conventional two-separate-member-type metal terminal member through a grommet.

At this time, as shown in FIG. 11(b), which will be described later, the forward end portions 43 of the rear metal terminal members 40 are fitted into the corresponding connection portions 23 of the forward metal terminal members 20, whereby the forward metal terminal members 20 and the rear metal terminal members 40 are connected respectively.

Next, the rear metal terminal member 40, which is a feature of the present invention, will be described with reference to FIGS. 8 to 12.

Figure 9A:
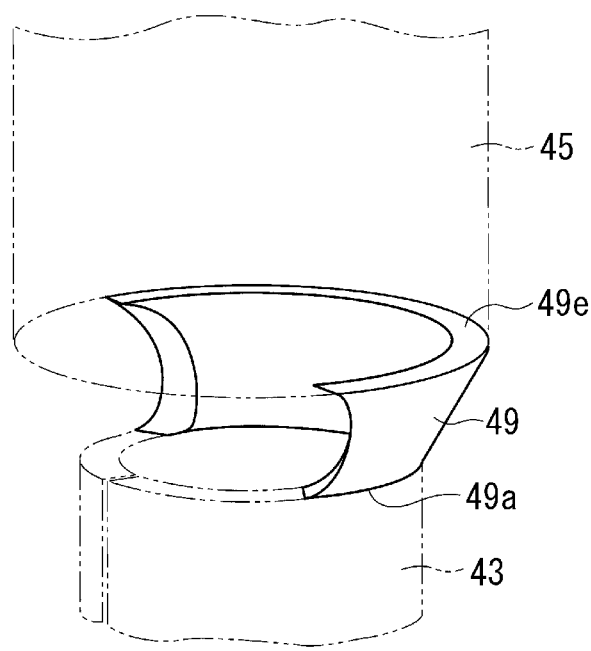
FIGS. 9(a) and 9(b) are views consisting of a perspective view and sectional view of a first neck portion.
Figure 9B:
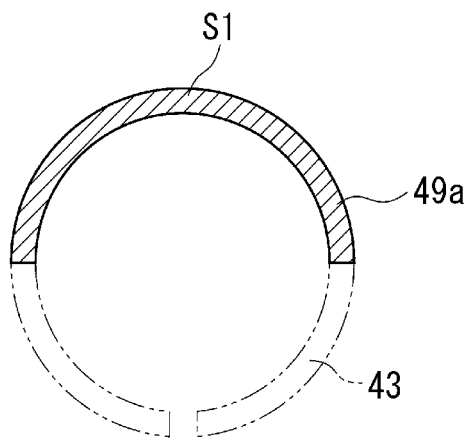
Figure 10A:
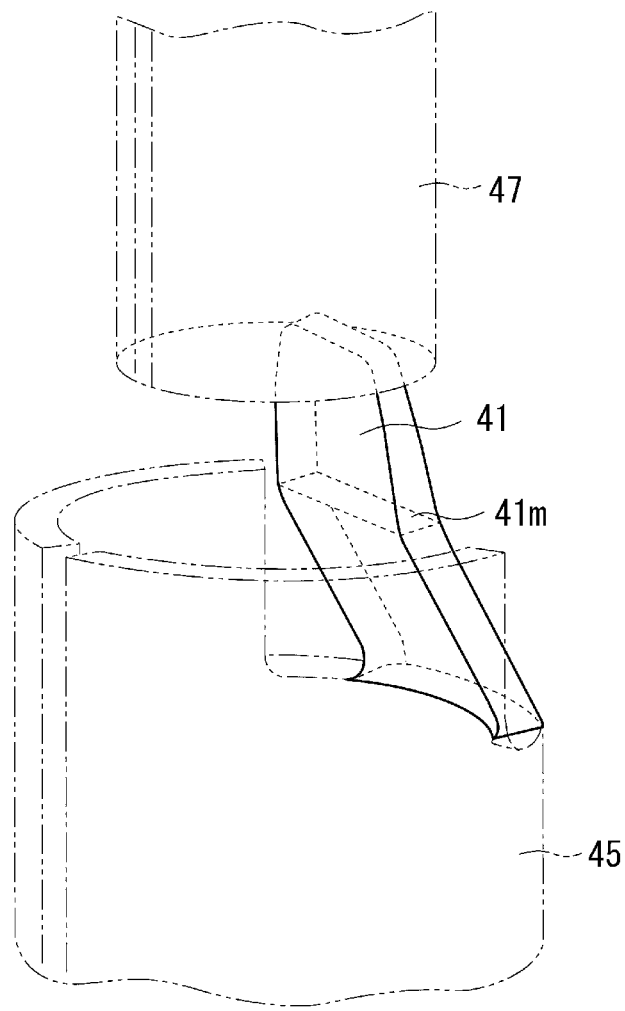
FIGS. 10(a) and 10(b) are views consisting of a perspective view and sectional view of a second neck portion.
Figure 10B:
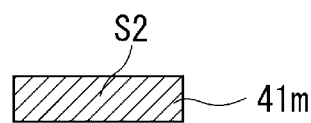

FIG. 8 is a side view of the rear metal terminal member 40; FIGS. 9(a) and 9(b) are views consisting of a perspective view and a sectional view of the first neck portion 49; FIGS. 10(a) and 10(b) are a perspective view and a sectional view of the second neck portion 41; and FIGS. 11(a) and 11(b) are views showing a step of connecting the forward metal terminal member 20 and the rear metal terminal member 40.

As shown in FIG. 9(a), the first neck portion 49 has an arc form such that the diameter reduces from a rear end portion 49e connected to the large-diameter portion 45 and having an arc section toward a forward end portion 49a connected to the forward end portion 43 and having an arc section. Therefore, the first neck portion 49 has the smallest sectional area at the forward end portion 49a. A section S1 of the forward end portion 49a taken along line C-C of FIG. 8 (a plane orthogonal to the direction of the axial line O) has such an arc form as to be a portion of the section of the forward end portion 43.

Notably, the area of the section S1 of that portion (the forward end portion 49a in the present embodiment) of the first neck portion 49 which has the smallest sectional area corresponds to "the sectional area orthogonal to the direction of the axial line (of the first neck portion)" appearing in claims. Theoretically, the axis of the rear separator 95 coincides with the axis of the sensor element 10. However, since there is misalignment or the like therebetween, calculation of the area of the section S1 employs the axis of the rear separator 95 as the axial line O. That is, in a state in which the rear metal terminal member 40 is held in the rear separator 95, the axial line O of the rear separator 95 is employed as a reference axis for calculating the sectional area of the first neck portion 49.

Similarly, as shown in FIG. 10(a), the second neck portion 41 has a generally flat-plate form and is bent obliquely (radially outward) from a back surface (the right side surface in FIG. 8) of the crimp terminal portion 47 toward a back side (the right side in FIG. 8) of the large-diameter portion 45. The second neck portion 41 has the smallest sectional area at a central portion 41m with respect to the direction of the axial line O, and a section S2 of the central portion 41m taken along line D-D of FIG. 8 (a plane orthogonal to the direction of the axial line O) has a rectangular shape.

Notably, the area of the section S2 of that portion (the central portion 41m in the present embodiment) of the second neck portion 41 which has the smallest sectional area corresponds to "the sectional area orthogonal to the direction of the axial line (of the second neck portion)" appearing in claims.

In the present invention, the sectional area of the first neck portion 49 is smaller than the sectional areas orthogonal to the direction of the axial line O of the forward end portion 43 and the large-diameter portion 45, and the sectional area of the second neck portion 41 is smaller than the sectional areas orthogonal to the direction of the axial line O of the large-diameter portion 45 and the crimp terminal portion 47.

Thus, the first neck portion 49 and the second neck portion 41 can be rendered lower in rigidity (moment of inertia of area) than the forward end portion 43, the large-diameter portion 45, and the crimp terminal portion 47, whereby a portion of the rear metal terminal member 40 susceptible to deformation can be adjusted by means of the first neck portion 49 and the second neck portion 41.

Notably, "the sectional areas" of the forward end portion 43, the large-diameter portion 45, and the crimp terminal portion 47 are the sectional areas of their portions connected to the first neck portion 49 and the second neck portion 41.

Further, the first neck portion 49 is greater in moment of inertia of area orthogonal to the direction of the axial line O than the second neck portion 41.

Thus, the first neck portion 49 can be rendered higher in rigidity than the second neck portion 41. As a result, as shown in FIGS. 11(a) and 11(b), in connecting the forward end portion 43 of the rear metal terminal member 40 to the connection portion 23 of the forward metal terminal member 20, there can be restrained difficulty in connection (insertion) which could otherwise result from a change in direction of the forward end portion 43 caused by bending of the first neck portion 49.

Meanwhile, the second neck portion 41 is lower in rigidity than the first neck portion 49. As a result, in the case where the crimp terminal portion 47 is misaligned from the large-diameter portion 45 and the forward end portion 43 with respect to the direction of the axial line O, excessive force may be applied to the lead wire 146 connected to the crimp terminal portion 47 within the insertion hole 95h of the rear separator 95. However, even in this case, since the second neck portion 41 is deformed radially as indicated by the arrow T of FIG. 11(b) to thereby mitigate the force, there can be restrained detachment of the lead wire 146 from the crimp terminal portion 47 and breakage of the lead wire 146.

According to the present embodiment, the lead wire 146 is connected beforehand to the rear metal terminal member 40 on the forward side of the rear separator 95, and subsequently, the lead wire 146 is pulled rearward to accommodate the rear metal terminal member 40 within the insertion hole 95h of the rear separator 95.

Even in such a case, since the second neck portion 41 is lower in rigidity than the first neck portion 49, even though excessive force is applied to the lead wire 146 connected to the crimp terminal portion 47 within the insertion hole 95h of the rear separator 95 when the lead wire 146 is pulled rearward, the second neck portion 41 is deformed radially as indicated by the arrow T of FIG. 11(b) to thereby mitigate the force.

In the present embodiment, diameter differs between the forward end portion 43 and the large-diameter portion 45, which are connected in the direction of the axial line O through the first neck portion 49. In this case, if, in metal working, expansion is attempted from the forward end portion 43 to the large-diameter portion 45 without provision of the first neck portion 49, wrinkles may appear or cracking may occur in the boundary between the forward end portion 43 and the large-diameter portion 45.

By means of the first neck portion 49 smaller in sectional area than the forward end portion 43 and the large-diameter portion 45 intervening between the portions 43 and 45, in the course of expansion from the forward end portion 43 to the large-diameter portion 45, the deformable first neck portion 49 absorbs wrinkles which would otherwise appear as a result of difference in diameter between the forward end portion 43 and the large-diameter portion 45, thereby restraining appearance of wrinkles or generation of crack in the forward end portion 43 and the large-diameter portion 45.

The second neck portion 41 also yields a similar working effect.

The moments of inertia of area of the first neck portion 49 and the second neck portion 41 can be calculated by analyzing the shapes of the section S1 of the first neck portion 49 and the section S2 of the second neck portion 41 on CAD (computer-aided design) software by use of mechanical element data. JIS-B3401 specifies CAD as "design in which a model defined by the shape of a product and other attribute data is formed within a computer, followed by analysis and processing." An example of CAD software is Solid Works.

The present invention requires mere comparison of the magnitude of moment of inertia of area between the first neck portion 49 and the second neck portion 41; therefore, employment of the same conditions in calculating the respective moments of inertia of area suffices. No particular limitation is imposed on specific conditions of calculation, a calculation program, and CAD software for calculation.

Notably, the actual rear metal terminal member 40 was calculated for the moments of inertia of area of the sections S1 and S2 having predetermined dimensions of the first neck portion 49 and the second neck portion 41 shown in FIGS. 9 and 10, respectively, by use of CAD software "Solid Works." The calculated moments of inertia of area of the sections S1 and S2 were 0.0921 mm$^4$ and 0.0007 mm$^4$, respectively.

As shown in FIGS. 8 and 10, in the present embodiment, the second neck portion 41 extends obliquely from the large-diameter portion 45 of the rear metal terminal member 40 and is connected to the crimp terminal portion 47. By virtue of this, the crimp terminal portion 47 is coaxial with the forward end portion 43 in the direction of the axial line O.

As a result, misalignment between the crimp terminal portion 47 and the forward end portion 43 with respect to the direction of the axial line O reduces, whereby excessive force is unlikely to be applied to the lead wire 146 connected to the crimp terminal portion 47 within the insertion hole 95h of the rear separator 95, thereby restraining detachment of the lead wire 146 from the crimp terminal portion 47 and breakage of the lead wire 146 to a greater extent.

Particularly, in the case where the lead wire 146 is connected beforehand to the rear metal terminal member 40 on the forward side of the rear separator 95; subsequently, the lead wire 146 is pulled rearward to accommodate the rear metal terminal member 40 within the insertion hole 95h of the rear separator 95, detachment and breakage of the lead wire 146 can be effectively restrained.

Notably, the reason for employment of the axis of the rear separator 95 as the axial line O is as mentioned above.

In the present embodiment, as shown in FIGS. 2 to 4, the connection portions 23 and 33 of the forward metal terminal members 20 and 30 assume the form of at least a portion 43 of a tube (a cylinder in the present embodiment), and the forward end portion of the rear metal terminal member 40 tapers off forward and is fitted into the connection portion 23 or 33.

Since the forward end portion 43 tapers off forward, the forward end portion 43 can be readily fitted into the tube of the connection portion 23 or 33, whereby the rear metal terminal member 40 and the forward metal terminal member 20 or 30 can be easily and reliably connected to each other.

Also, in the present embodiment, as shown in FIGS. 2 to 4, the forward end portion 43 of the rear metal terminal member 40 assumes the form of at least a portion of a cylindrical tube, and the connection portions 23 and 33 of the forward metal terminal members 20 and 30 assume the form of at least a portion of a cylindrical tube.

As mentioned above, since the connection portions 23 and 33 and the forward end portion 43 are of rotational symmetry about the axial line O, even though the rear metal terminal member 40 and the forward metal terminal member 20 or 30 are positionally deviated about the axial line O to some extent, the forward end portion 43 can be fitted into the connection portion 23 or 33, whereby the rear metal terminal member 40 and the forward metal terminal member 20 or 30 can be easily and reliably connected to each other.

The present invention is not limited to the above embodiment, but extends into various modifications and equivalents encompassed by the ideas and scope of the invention.

The metal terminal member and the separator are not limited in shape, etc., to those of the above embodiment. The separator may not be divided into the forward separator and the rear separator, but may assume the form of a single member.

The connection (coupling) structure between the rear metal terminal member and the forward metal terminal member is not limited to the above, but may be, for example, as follows: a rear end portion of the forward metal terminal member may have the shape of a male pin, and the male pin may be fitted into a tubular forward end portion of the rear metal terminal member.

In the case where a rear end portion of the forward metal terminal member and a forward end portion of the rear metal terminal member assume a tubular form, the tubular form is not limited to a cylindrical tube, but may be a prismatic tube such as a square tube. The tubular form may not be a completely closed tube, but may be at least a portion of a tube (may have a C-shaped section, for example). The tube of the forward metal terminal member or the rear metal terminal member may be replaced with a circular column or a portion of the circular column.

In the above embodiment, the large-diameter portion 45, or a central portion, of the rear metal terminal member is greater in diameter than the forward end portion 43 and the lead-wire connection portion 47, and the rear end face 45e of the large-diameter portion 45 is used for positioning in relation to the rear separator 95. However, the present invention is not limited thereto. The central portion may have the same diameter as that of the forward end portion or the lead-wire connection portion, or the central portion may be smaller in diameter than the forward end portion and the lead-wire connection portion.

By virtue of provision of the central portion, the forward end portion and the lead-wire connection portion can be connected through the central portion with two neck portions provided before and after, respectively, the central portion. By adjusting rigidities of the two neck portions, the above-mentioned effect is yielded. Therefore, no particular limitation is imposed on the shape and dimensions of the central portion so long as the effect is yielded.

Examples of the gas sensor include, in addition to an $NO_x$ sensor, an oxygen sensor and a full range gas sensor.

DESCRIPTION OF REFERENCE NUMERALS

1: gas sensor
10: sensor element
11a: electrode pad
20, 30: forward metal terminal member
23, 33: connection portion of forward metal terminal member
40: rear metal terminal member
41: second neck portion
43: forward end portion of rear metal terminal member
45: central portion (large-diameter portion) of rear metal terminal member
47: lead-wire connection portion of rear metal terminal member
49: first neck portion
90: separator (forward separator)
95: separator (rear separator)
146: lead wire
O: axial line
S1: section orthogonal to axial direction of first neck portion
S2: section orthogonal to axial direction of second neck portion

What is claimed is:

1. A gas sensor comprising:
    a sensor element extending in a direction of an axial line and including a rear end portion having an outer surface, and an electrode pad on the outer surface;
    a metal terminal member extending in the direction of the axial line and including:
        a forward metal terminal member electrically connected to the electrode pad and including a rear-end connection portion; and
        a rear metal terminal member including a forward end portion connected to the rear-end connection portion of the forward metal terminal member in an overlapping manner, a central portion located rearward of the forward end portion, and a lead-wire connection portion located rearward of the central portion;
    a tubular separator which holds the metal terminal member and surrounds the rear end portion of the sensor element; and
    a lead wire including a distal end portion connected to the lead-wire connection portion of the rear metal terminal member, and extending rearward of the tubular separator,
    wherein the forward end portion of the rear metal terminal member and the central portion of the rear metal terminal member are integrally connected through a first neck portion smaller in sectional area orthogonal to the direction of the axial line than the forward end portion of the rear metal terminal member and the central portion of the rear metal terminal member, and the central portion of the rear metal terminal member and the lead-wire connection portion of the rear metal terminal member are integrally connected through a second neck portion smaller in sectional area orthogonal to the direction of the axial line than the central portion of the rear metal terminal member and the lead-wire connection portion of the rear metal terminal member, and
    the first neck portion is greater in moment of inertia of area orthogonal to the direction of the axial line than the second neck portion.

2. The gas sensor according to claim 1, wherein the forward end portion and the lead-wire connection portion of the rear metal terminal member are coaxial in the direction of the axial line.

3. The gas sensor according to claim 1, wherein the rear-end connection portion of the forward metal terminal member is tube-like, and the forward end portion of the rear metal terminal member tapers forward and fits into the rear-end connection portion.

4. The gas sensor according to claim 1, wherein the forward end portion of the rear metal terminal member is cylinder-like, and the rear-end connection portion of the forward metal terminal member is cylinder-like and receives the forward end portion of the rear metal terminal member.

* * * * *